(12) United States Patent
Reece et al.

(10) Patent No.: US 8,828,924 B2
(45) Date of Patent: Sep. 9, 2014

(54) METHODS OF TREATING A DIABETIC EMBRYOPATHY

(75) Inventors: E. Albert Reece, Baltimore, MD (US); Zhiyong Zhao, Ellicott City, MD (US); Peixin Yang, Woodstock, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 163 days.

(21) Appl. No.: 12/779,935

(22) Filed: May 13, 2010

(65) Prior Publication Data

US 2010/0291069 A1 Nov. 18, 2010

Related U.S. Application Data

(60) Provisional application No. 61/178,227, filed on May 14, 2009.

(51) Int. Cl.
| | | |
|---|---|---|
| *A61K 38/00* | (2006.01) | |
| *A61K 31/5377* | (2006.01) | |
| *A61K 31/415* | (2006.01) | |
| *A61K 31/4545* | (2006.01) | |
| *A61K 38/18* | (2006.01) | |
| *A61K 38/44* | (2006.01) | |
| *A61K 31/506* | (2006.01) | |
| *A61K 31/40* | (2006.01) | |
| *A61K 31/445* | (2006.01) | |
| *A61K 39/00* | (2006.01) | |

(52) U.S. Cl.
CPC ............. *A61K 31/40* (2013.01); *A61K 31/5377* (2013.01); *A61K 31/415* (2013.01); *C12Y 103/01024* (2013.01); *A61K 31/4545* (2013.01); *A61K 38/1808* (2013.01); *A61K 38/44* (2013.01); *A61K 2039/505* (2013.01); *A61K 31/506* (2013.01); *A61K 38/1825* (2013.01); *A61K 31/445* (2013.01)
USPC ......................................................... 514/1.1

(58) Field of Classification Search
USPC ........................................................ 514/1.1
See application file for complete search history.

(56) References Cited

U.S. PATENT DOCUMENTS

| 7,438,933 | B2 | 10/2008 | Wu et al. | |
|---|---|---|---|---|
| 2005/0148650 | A1 | 7/2005 | Ohkawa et al. | |
| 2005/0261247 | A1* | 11/2005 | Hotamisligil et al. | 514/81 |
| 2006/0019910 | A1* | 1/2006 | Greenberg | 514/44 |
| 2006/0128714 | A1* | 6/2006 | Wu et al. | 514/251 |
| 2007/0167386 | A1 | 7/2007 | Otsu et al. | |
| 2008/0033022 | A1 | 2/2008 | Salituro et al. | |
| 2008/0039377 | A1 | 2/2008 | Rommel et al. | |
| 2008/0255222 | A1 | 10/2008 | Halazy et al. | |
| 2008/0287458 | A1 | 11/2008 | Abbot et al. | |
| 2009/0054438 | A1 | 2/2009 | Ronai et al. | |

FOREIGN PATENT DOCUMENTS

WO WO 2005/058298 * 6/2005

OTHER PUBLICATIONS

Perrin et al. (BMC Medicine 2007, 5:25 1-7).*
Yoshioka (Circulation 2004, 109:2581-2586).*
Yoshida (Redox Signal. 5, 563-570).*
Saitoh et al (The EMBO Journal vol. 17 No. 9 pp. 2596-2606, 1998).*
Ozawa et al (Reproduction, Fertility and Development 18(2) 194-194).*
Filomeni et al., Disulfide relays and phosphorylative cascades: partners in redox-mediated signaling pathways, Cell Death and Differentiation, 12, 1555-1563, 2005.*
Song et al., Differential role of glutaredoxin and thioredoxin in metabolic oxidative stress-induced activation of apoptosis signal-regulating kinase 1,Biochem. J. 378, 845-853, 2003.*
Thandavarayan et al., 14-3-3 protein regulates Ask1 signaling and protects against diabetic cardiomyopathy, Biochem. Pharmacol., 75, 1797-1806, 2008).*
KMom (1999); 20 pages.*
Fetita et al. The Journal of Clinical Endocrinology & Metabolism 91(10):3718-3724, (2006).*
Bennett, Brydon et al., "JNK; A New Therapeutic Target for Diabetes," Curr Opin in Pharmacology 2003, vol. 3, pp. 420-425.
Bhuiyan et al., "Targeting Protein Kinase B/Akt Signaling With Vanadium Compounds For Cardioprotection," Expert Opinion 2008, vol. 12 (10), pp. 1217-1227.
Bozinovski et al., "The Synthetic Peptide RPRAATF Allows Specific Assay of Akt Activity in Cell Lysates," Analytical Biochemistry 2002, vol. 305, pp. 32-39.
Buchwald et al., "Long-Term, Continuous Intravenous Heparin Administration by an Implantable Infusion Pump in Ambulatory Patients with Recurrent Venous Thrombosis," Surgery 1980, vol. 88, pp. 507-516.
Cenni, Vittoria et al., "Lamin A Ser404 Is a Nuclear Target of Akt Phosphorylation in C2C12 Cells," J of Proteome Research 2008, vol. 7(11), pp. 4727-4735.
Cho, Ssang-Goo et al., "Glutathione S-Transferase Mu Modulates the Stress-activated Signals by Suppressing Apoptosis Signal-regulating Kinase 1,"—J of Biological Chem 2001, vol. 16, pp. 12749-12755.
Cho, Ssang-Goo et al., "Identification of a Novel Antiapoptotic Protein That Antagonizes ASK1 and CAD Activities," J of Cell Biol 2003, vol. 163 (1), pp. 71-81.
During, et al., "Controlled Release of Dopamine from a Polymeric Brain Implant: In Vivo Characterization,"—Annals of Neurology 1989, vol. 25, pp. 351-356.
Elghazi, L. et al., "Regulation of Beta-cell Mass and Function by the Akt/Protein Kinase B signalling Pathway," Diabetes, Obesity and Metabolism 2007, vol. 9 (Suppl 2), pp. 147-157.

(Continued)

*Primary Examiner* — Shirley V Gembeh
(74) *Attorney, Agent, or Firm* — Kristina Castellano; Castellano PLLC

(57) ABSTRACT

Maternal diabetes can lead to a developmental malformation of an embryo. A developmental malformation caused by maternal diabetes is commonly referred to as a diabetic embryopathy. There is currently no effective treatment for reducing or inhibiting a diabetic embryopathy. To this end, the present invention is drawn to novel methods of treating a diabetic embryopathy.

10 Claims, 4 Drawing Sheets

(56) References Cited

OTHER PUBLICATIONS

Franke, Thomas, "Akt-interacting Proteins: Attractive Opposites. Focus on Carboxy-terminal Modulator Protein Induces Akt Phosphorylation and Activation, Thereby Enhancing Antiapoptotic, Glycogen Synthetic, and Glucose Uptake Pathways," American J Physiol Cell Physiol—Dec. 2007, vol. 293, pp. 1768-1770.

Ghose, "A Knowledge-Based Approach in Designing Combinatorial or Medicinal Chemistry Libraries for Drug Discovery. 1. A Qualitative and Quantitative Characterization of Known Drug Databases," J Comb Chem 1999, vol. 1, pp. 55-68.

Goodson, Max, "Dental Applications,"—Medical Appls of Controlled Release, vol. II, 1984, pp. 115-138.

Harding, Thomas et al., "Inhibition of JNK by Overexpression of the JNK Binding Domain of JIP-1 Prevents Apoptosis in Sympathect Neurons," J of Biol Chemistry 2001, vol. 276 (7), pp. 4531-4534.

Hemstrom, Therese et al., "Inhibitors of the PI3-kinase/Akt pathway induce mitotic catastrophe in non-small cell lung cancer cells,"—Int J Cancer 2006, vol. 119, pp. 1028-1038.

Hines, et al., "Coexpression of c-kit and stem cell factor in breast cancer results in enhanced sensitivity to members of the EGF family of growth factors," Susan et al—Breast Cance Research & Treat 1999, vol. 58, pp. 1-10.

Howard et al., "Intracerebral Drug Delivery in Rats with Lesion-Induced Memory Deficits," J of Neurosurgery 1989, vol. 71, pp. 105-112.

Hsu, Ming-Chuan et al., "HER-2/neu Transcriptionally Activates Jab1 Expression via the AKT/beta-catenin Pathway in Breast Cancer Cells," Endocrine-Related Cancer 2007, vol. 14, pp. 655-667.

Kalluri et al., "Mechanism of Insulin-like Growth Factor I-mediated Proliferation of Adult Neural Progenitor Cells: Role of Akt,"—EP J of Neuroscience 2007, vol. 25, pp. 1041-1048.

Kim, Jee-Youn et al., "The Critical Role of ERK in Death Resistance and Invasiveness of Hypoxia-selected Glioblastoma Cells," BMC Cancer 2009, pp. 9-27.

Langer, "New Methods of Drug Delivery," Science (Sep. 1990), vol. 249, pp. 1527-1533.

Langer & Peppas, "Chemical and Physical Structure of Polymers as Carriers for Controlled Release of Bioactive Agents: A Review," J Macromol Sci Review Macromol Chem 1983, vol. 23, pp. 61-126.

Lerner-Marmarosh, N. et al., "Human Biliverdin Reductase is an ERK Activator; hBVR is an ERK Nuclear Transporter and is Required for MAPK Signaling," PNAS (May 13, 2008), vol. 19, pp. 6870-6875.

Levy et al., "Inhibition of Calcification of Bioprosthetic Heart Valves by Local Controlled Release Diphosphonate," Science 1985, vol. 228, pp. 190-192.

Li, Yuchi et al., "Inhibition of c-Jun N-Terminal Kinase Pathway Improves Cell Viability in Response to Oxidant Injury," Amer J Respir Cell Mol Biol 2003, vol. 29, pp. 779-783.

Lin, Anning, "Activation of the JNK Signaling Pathway: Breaking the Brake on Apoptosis," Bioessays 2003, vol. 25, pp. 17-24.

Lipinsky et al., "Experimental and Computational Approaches to Estimate Solubility and Permeability in Drug Discovery and Development Settings," Advanced Drug Del Reviews 1997, vol. 23, pp. 3-25.

Lipinski et al., "Experimental and computational approaches to estimate solubility an permeability in drug discovery and development settings,"—Advanced Drug Del Reviews 2001, vol. 46, pp. 3-26.

Minden, et al., "Regulation and function of the JNK subgroup of MAP kinases,"—Biochimica et Biophysica Acta 1997, vol. 1333, pp. F85-F103.

Nakazawa, T. et al., "Intravitreal administration of N-Methyl-D-Aspartate (NMDA) induces cell death both in the ganglion and amacrine cells with the suppression of protein kinase B (Akt) activity,"—Invest Ophthalmol Vis Sci 2004, 45, E-Abstract 872.

Oprea, T. I., et al., "Is there a Difference Between Leads and Drugs? A Historical Perspective,"—J Chem Info Comput Sci 2001, vol. 41, pp. 1308-1315.

Reece, E. et al., "Dietary Vitamin and Lipid Therapy Rescues Aberrant Signaling and Apoptosis and Prevents Hyperglycemia-induced diabetic embryopathy in rats,"—Amer J Obstetrics & Gyn 2006, vol. 194, pp. 580-585.

Reece, E.A. et al., "Aberrant patterns of cellular communication in diabetes-induced embryopathy I. Membrane signalling,"—J of Maternal-Fetal & Neonatal Med 2002, vol. 11, pp. 249-253.

Saudek et al., "A Preliminary Trial of the Programmable Implantable Medication System for Insulin Delivery,"—New England J of Med 1989, vol. 321, pp. 574-579.

Tang, et al., "Akt (Protein Kinase B) and Retinal Ganglion cell survival in retinal Ischemia-reperfusion Injury in rats"—Invest Ophthalmol Vis Sci 2002, 43, E-Abstract 772.

Tobiume, K. et al., "ASK1 is required for sustained activations of JNK/p38 MAP kinases and apoptosis,"—EMBO Reports 2001, pp. 222-228.

Tobiume, K. et al., "Activation of Apoptosis Signal-Regulating Kinase 1 by the Stress-Induced Activating Phosphorylation of Pre-Formed Oligomer,"—J of Cellular Physiol 2002, vol. 191(1), pp. 95-104.

Tournier, et al., "Requirement of JNK for Stress-Induced Activation of the cytochrome c-mediated Death Pathway," 2003, vol. 288, pp. 870-874.

Treat et al., "Liposome Encapsulated doxorubicin Preliminary Results of Phase I and Phase II Trials", Liposomes in the Therapy of Infectious Diseases & Cancer 1988, pp. 353-369.

Yang, "ERK activation by urea in the renal inner medullary mIMcD3 cell line," Xiao-Yan et al—Am J Physiol Renal Physiol 1999, pp. F176-F185.

* cited by examiner

METHODS OF TREATING A DIABETIC EMBRYOPATHY

CROSS-REFERENCE TO RELATED APPLICATION

This application claims the benefit of U.S. provisional application 61/178,227, filed on May 14, 2009.

STATEMENT OF FEDERALLY SPONSORED RESEARCH AND DEVELOPMENT

This invention was made with government support under the Grant Number HD043489 awarded by the National Institutes of Health. The government has certain rights in the invention.

TECHNICAL FIELD

The present invention relates generally to the study of congenital malformation. More specifically, the present invention relates to methods of treating a diabetic embryopathy.

BACKGROUND OF INVENTION

Each year in the United States, more than 150,000 babies are born with a major congenital malformation. This problem is worse in offspring of women who have poorly controlled type 1 or 2 diabetes during pregnancy; 6%-10% of these babies are born with a major congenital malformation. Based on the National Health and Nutrition Examination Survey conducted during 1988-1994, 1.1% of women 20-39 years of age have type 1 or 2 diabetes, and the incidence of diabetes among women of childbearing age has been increasing over the past four decades. It is projected that the number of women of childbearing age with type 2 diabetes will double by 2010, suggesting that without intervention approximately 8,000 babies will be born each year in the United States with a congenital malformation secondary to type 1 or 2 diabetes.

Human observational studies have demonstrated a strong link between the extent of a mother's glycemic control and the incidence of congenital malformations in her offspring. The putative teratogenic effects of hyperglycemia are supported by studies that demonstrate a reduction in the incidence of birth defects following clinical intervention targeted at achieving euglycemia. When euglycemia is successfully maintained periconceptionally and during the first trimester, the prevalence of malformations is reduced to a level comparable to that of the general population. However, even with excellent compliance and clinical care, euglycemia may be difficult to achieve and maintain. In addition, it is possible that organogenesis can be affected by short periods of hyperglycemia that are not reflected in the averaged values of glycosylated hemoglobin levels, which are used to monitor glucose levels. A further obstacle is that most women with diabetes do not seek pre-pregnancy care and most have unplanned pregnancies. Hence, a very important goal for public health is to develop and implement accessible and affordable intervention strategies to diminish the occurrence of these anomalies.

Both clinical cases and animal studies have clearly demonstrated that the main characteristics of maternal hyperglycemia-associated defects are abnormal organogenesis and underdevelopment. The organ systems most commonly affected include the central nervous, cardiovascular, gastrointestinal, craniofacial, genitourinary, and skeletal systems. Because the heart and the neural tube develop early during embryogenesis, a higher incidence of malformations is often seen in these two organs. In the central nervous system, abnormalities can be categorized as underdevelopment of the midbrain and hindbrain and failure of the neural tube to close at both anterior (rostral) and posterior (caudal) ends of the neural axis. The failure of posterior neural tube closure results in spina bifida, a common birth defect seen in newborns.

Considering the need in the art for compositions and methods for treating a diabetic embryopathy, it is desirable to define an optimal intervention strategy for treating a diabetic embryopathy. The present invention fulfils this long-felt need and desire in the art.

BRIEF SUMMARY OF INVENTION

The invention relates to methods of treating a diabetic embryopathy. By way of example, the invention relates to methods for treating a diabetic embryopathy comprising administering to a mammal in need thereof a modulator of an activity of a polypeptide involved in cell signaling that is altered during maternal diabetes and/or participates in the pathology of a diabetic embryopathy.

The invention also relates to methods of treating diabetic embryopathy that include administering to a mammal in need thereof at least one agent that modulates the activity of at least one polypeptide selected from the group consisting of apoptosis signal-regulating kinase 1 (ASK1), c-Jun N-terminal kinases (JNK), extracellular signal-regulated kinase (ERK) (such as ERK1 and ERK2), and Akt.

In certain embodiments, the invention is drawn to a method of treating a diabetic embryopathy consisting of, consisting essentially of, or comprising administering an agent that modulates the activity of the polypeptide apoptosis signal-regulating kinase 1 (ASK1). In other embodiments, an agent that modulates the activity of ASK1 decreases the activity of ASK1.

In certain embodiments, the invention is drawn to a method of treating a diabetic embryopathy consisting of, consisting essentially of, or comprising administering an agent that modulates the activity of the polypeptide c-Jun N-terminal kinases (JNK). In other embodiments, an agent that modulates the activity of JNK decreases the activity of JNK. In further other embodiments, JNK is JNK1, JNK2, or JNK3. In even further other embodiments, JNK is JNK1 or JNK2.

In certain embodiments, the invention is drawn to a method of treating a diabetic embryopathy consisting of, consisting essentially of, or comprising administering an agent that modulates the activity of the polypeptide extracellular signal-regulated kinase (ERK). In other embodiments, an agent that modulates the activity of ERK increases the activity of ERK. In example embodiments, ERK is ERK1 or ERK2.

In certain embodiments, the invention is drawn to a method of treating a diabetic embryopathy consisting of, consisting essentially of, or comprising administering an agent that modulates the activity of a polypeptide of the Akt family. In other embodiments, an agent that modulates the activity of a polypeptide of the Akt family increases the activity of a polypeptide of the Akt family. In further embodiments, a polypeptide of the Akt family is Akt1, Akt2, and Akt3.

Example embodiments also include methods that include administering to a mammal in need thereof at least one agent that modulates the activity of at least one polypeptide selected from the group consisting of ASK, JNK, ERK and Akt; and providing or administering a multi-nutrient supplement regimen to the mammal.

The foregoing has outlined rather broadly the features and technical advantages of the present invention in order that the detailed description of the invention that follows may be better understood. Additional features and advantages of the invention are described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth herein. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
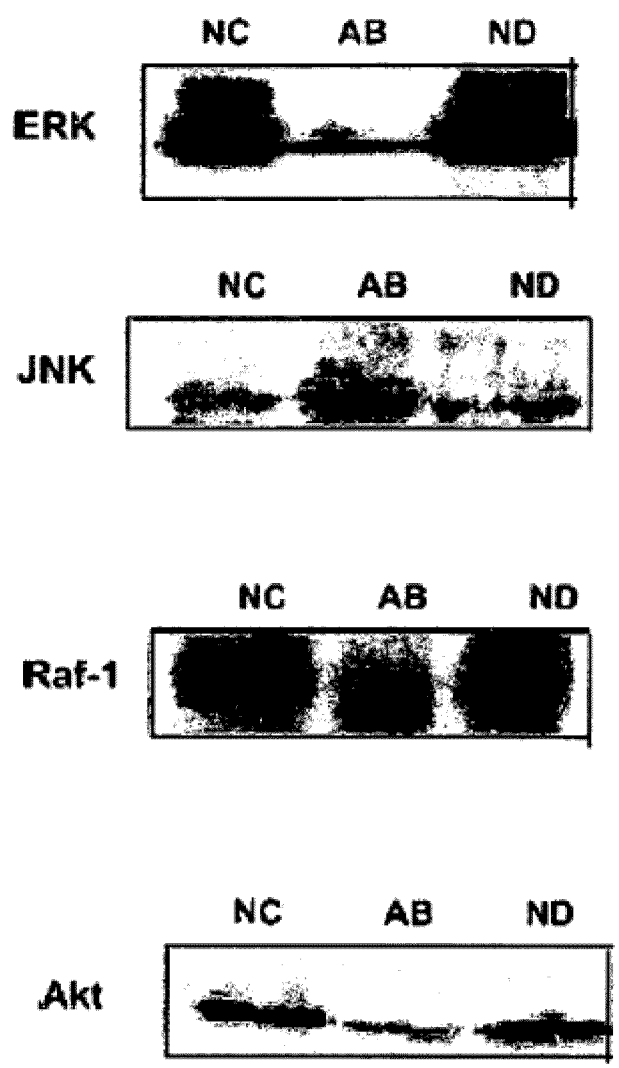
FIG. 1. Western blots illustrating changes in levels of phosphorylated ERK1/2, JNK1/2 Raf-1 and Akt from yolk sacs. NC: non-diabetic control; AB: abnormal embryo from diabetic; and ND: normal embryo from diabetic.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "agent" is a molecular entity including, for example, a small molecule (especially small organic molecules that satisfy the constraints of Lipinski's Rules (Lipinski, C. A. et al. (1997) "Experimental And Computational Approaches To Estimate Solubility And Permeability In Drug Discovery And Development Settings," Adv. Drug Del. Rev, 23:3-25; Lipinski, C. A. et al. (2001) "Experimental And Computational Approaches To Estimate Solubility And Permeability In Drug Discovery And Development Settings," Adv. Drug Del. Rev. 46, 3-26; Oprea, T. I. et al. (2001) "Is There A Difference Between Leads And Drugs? A Historical Perspective," J. Chem. Inf. Comput. Sci. 41:1308-1315; Amp, K. et al. (1999) "A Knowledge-Based Approach in Designing Combinatorial or Medicinal Chemistry Libraries for Drug Discovery," J. Combin. Chem. 1:55-68), a nucleic acid (e.g., an oligonucleotide, and in particular, a siRNA, a shRNA, an expression cassette, an antisense DNA, an antisense RNA, etc.), protein, peptide, antibody, antisense drug, or other biomolecule that is naturally made, synthetically made, or semi-synthetically made and is used alone or in combination with other therapies or methods to treat a diabetic embryopathy. In particular aspects of invention, an agent is a small molecule that modulates the activity of ASK1, JNK, ERK (such as ERK1 or ERK2), or Akt, and is useful for treating a diabetic embryopathy, each of which may be used alone or in conjunction with one another in any combination of the agents described herein.

As used herein, a "diabetic embryopathy" and all its forms and tenses (including, for example, diabetes-induced embryopathy and diabetes-associated embryopathy) refer to a myriad of pathological abnormalities, anomalies, or malformations (including, for example, a congenital malformation) resulting from maternal diabetes during gestation.

As used herein, "modulator" or "modulate" and all their forms and tenses (including, for example, modulation, modulating and modulated) refer to an agent that acts (or the act itself) to alter, adjust, or keep in proper measure or proportion a cellular event (including, for example, cell signaling and cell function). For example, a modulator of an activity of a polypeptide involved in cell signaling includes altering, adjusting, or keeping in proper measure the activity of the polypeptide such that cell signaling and cell function is normal and proper (i.e., there is a lack of cell pathology or dysfunction).

As used herein, "treat" and all its forms and tenses (including, for example, treating, treated, and treatment) refer to therapeutic treatment and prophylactic or preventative treatment (i.e., reducing, inhibiting, or preventing) for a subject in need thereof. A method of treating a diabetic embryopathy includes, for example, reducing or inhibiting the severity or occurrence of a diabetic embryopathy. A subject in need thereof includes a subject already with a pathological condition of the invention (including, for example, a diabetic embryopathy) as well as a subject in which a pathological condition of the invention is to be prevented. Subjects may include for example, mammals, and in particular may include humans. By way of example, mammals in need of treatment may include human females who are or may become pregnant. By way of further example, mammals in need of treatment may be human females who are or may become pregnant, in which the female has Type I, Type II, and/or Type III diabetes, in which case the female may be more likely than non-diabetic females to have an embryo with a diabetic embryopathy. Thus, by way of example, the mammal in need of the agent, or in need of treatment for diabetic embryopathy, may include the adult pregnant mammal, and the mammals being treated may include the adult and/or the embryo or fetus being carried (or who will be carried) by the adult.

II. The Present Invention

Kinases and Diabetic Embyropathy

Convincing evidence from clinical and experimental studies demonstrate that diabetes-related hyperglycemia leads to sustained generation of reactive oxygen species (ROS) and depletion of antioxidant defense that can result in intracellular oxidative stress due to an imbalance in intracellular reduction-oxidation (redox) homeostasis. Under normal physiological conditions, oxygen free radicals, including hydroxyl radicals, superoxide anions, singlet oxygen, and hydrogen peroxide ($H_2O_2$), are produced during cellular energy metabolism in subcellular organelles, including, for example, mitochondria. ROS mediated intracellular signal transduction regulates a wide range of cell functions, including proliferation, differentiation, and migration. However, under pathological conditions, excess reactive oxygen species can oxidize proteins, lipids, and DNA, causing cell dysfunction, cell injury, and even cell death.

Methods are provided herein that include administering to a mammal in need thereof, for example for the treatment of diabetic embryopathy, a modulator of an activity of a polypeptide involved in cell signaling that is altered during maternal diabetes or participates in the pathology of a diabetic embryopathy.

Example methods provided herein include administering to a mammal in need thereof at least one agent that modulates the activity of at least one polypeptide selected from the group consisting of apoptosis signal-regulating kinase 1 (ASK1), c-Jun N-terminal kinases (JNK), extracellular signal-regulated kinase (ERK), and Akt. As discussed further below, example agents may include at least one agent that decreases the activity of at least one polypeptide selected from the group consisting of ERK ASK1, JNK, and a polypeptide of the Akt family.

Further example agents may include at least one agent that increases the activity of at least one polypeptide selected from the group consisting of ERK ASK1, JNK, and a polypeptide of the Akt family.

Protein kinases are known signaling intermediates to mediate oxidative stress-induced apoptosis. Among the kinases, c-Jun N-terminal kinases (JNKs) are prominent ones that mediate oxidative stress-induced apoptosis in variety of cellular systems. The specific molecular targets of JNK include, for example, transcription factor AP-1 and non-transcription factors such as, for example, Bcl-2 family members (A. Minden and M. Karin, Biochim. Biophys. Acta 1333 (1997), pp. F85-F104; A. Lin, Bioessays 25 (2003), pp. 17-24). Substantial genetic and pharmacological data provide strong support to indicate that JNKs serve as important pro-apoptotic factors in cells undergoing oxidative stress (Tournier et al., Science 288 (2000), pp. 870-874; Tobiume et al. J. Cell Physiol. 191 (2002), pp. 95-104; Li et al., Am. J. Respir. Cell Mol. Biol. 29 (2003), pp. 779-783). Mitochondria are a site of action for JNK in apoptosis and the pro-apoptotic activity of JNK can be mediated by regulation of Bcl-2 family members. In maternal diabetes, JNK1/2 activation in the embryos and yolk sacs correlates with an increase in Bax expression and excessive apoptosis, leading to embryonic dysmorphogenesis (Reece et al., J. Matern. Fetal Neonatal Med. 11 (2002), pp. 249-253).

In addition, with antioxidant supplementation, the activation of JNK is blocked in the embryos and yolk sacs from diabetic rats, resulting in the prevention of diabetic embryopathy (Reece et al., Am. J. Obstet. Gynecol. 194 (2006), pp. 580-585). An increase in ROS production in the presence of oxidative stress specifically phosphorylates and thus activates ASK1, an upstream kinase of MAPKs (MAP kinase kinase kinase). This cascade of phosphorylation/activation in turn activates SEK1 (Jun kinase kinase) and ultimately results in JNK activation (Tobiume et al., EMBO Rep. 2 (2001), pp. 222-228). Considering this, one aspect of the invention is the discovery and use of an agent that decreases the activity of ASK1 and/or JNK (including, for example, JNK1 and JNK2) to treat a diabetic embryopathy.

In certain aspects of the invention drawn to an agent that modulates the activity of ASK1, modulation of ASK1 comprises decreasing the activity of ASK1. In further certain aspects, modulation of ASK1 consists of decreasing the activity of ASK1. In other further certain aspects, the agent that modulates the activity of ASK1 is effective for treating a diabetic embryopathy. In certain aspects, an agent that modulates the activity of ASK1 includes, for example, thioredoxin and other ASK1 inhibitors (US Patent Application Publication No. 20070167386); thioredoxin reductase; caspase-activated DNase (CAD) inhibitor that interacts with ASK1 (CIIA) (Cho et al., J. Cell Biol. 2003 Oct. 13; 163(1):71-81); glutathione S-transferase mu (J. Biol. Chem., Vol. 276, Issue 16, 12749-12755); and an antagonist anti-ASK1 antibody.

In certain aspects of the invention drawn to an agent that modulates the activity of JNK, modulation of JNK comprises decreasing the activity of JNK. In further certain aspects, modulation of JNK consists of decreasing the activity of JNK. In other further certain aspects, the agent that modulates the activity of JNK is effective for treating a diabetic embryopathy. In certain aspects, an agent that modulates the activity of JNK includes, for example, SP600125 (anthra[1-9cd]pyrazol-6(2H)-one; US Patent Application Publication No. 20090054438); JNK-interacting-protein-1 (JIP1; Harding et al., Journal Of Biological Chemistry 2001, 276(7):4531-4534); an antagonist anti-JNK antibody; 4-chloro-N-(3-{[4-(hexylamino)-1-piperidinyl]sulfonyl}phenyl)benzamide, 4-chloro-N-{4-[(4-{[4-(trifluoromethyl)benzyl]amino}-1-piperidin-yl)sulfonyl]phenyl}benzamide, 4-chloro-N-(4-{[4-({2-[3-(trifluoromethyl)phenyl]ethyl}amino)-1-piperidinyl]sulfonyl}phenyl)benzamide, 4-chloro-N-(4-{[4-(hexylamino)-1-piperidinyl]sulfonyl}benzyl)benzamide, 4-chloro-N-(4-{[4-(hexylamino)-1-piperidinyl]sulfonyl}phenyl)benzamide, 4-chloro-N-(3-{[4-(hexylamino)-1-piperidinyl]sulfonyl}benzyl)-benzamide, 4-chloro-N-{3-[(4-{[4-(trifluoromethyl)benzyl]amino}-1-piperidinyl)sulfonyl]benzyl}benzamide, 4-chloro-N-(3-{[4-({2-[3-(trifluoromethyl)phenyl]ethyl}amino)-1-piperidinyl]sulfonyl)benzyl)benzamide, 4-chloro-N-(4-{[4-({2-[3-(trifluoromethyl)phenyl]ethyl}amino)-1-piperidinyl]sulfonyl}benzyl)benzamide, 4-chloro-N-(3-{[3-(hexylamino)-1-pyrrolidinyl]sulfonyl}phenyl)benzamide, 4-chloro-N-{4-[(4-{[4-(trifluoromethyl)benzyl]amino}-1-piperidinyl)sulfonyl]benzyl}benzamide, 4-chloro-N-(3-{[3-({2-[3-(trifluoromethyl)phenyl]ethyl}amino)-1-pyr-rolidinyl]sulfonyl}phenyl)benzamide, N-(4-{[4-(butylamino)-1-piperidinyl]sulfonyl}benzyl)-2-oxo-1,2-dihy-dro-3-pyridinecarboxamide, 4-chloro-N-{4-[(3-{[4-(trifluoromethyl)benzyl]amino}-1-pyrrolidinyl-)sulfonyl]phenyl}benzamide, 4-chloro-N-{4-[(3-{[2-[3-(trifluoromethyl)phenyl]ethyl}amino)}-1-pyrrolidinyl)sulfonyl]phenyl}benzamide, 4-chloro-N-{3-[(4-{[4-(trifluoromethyl)benzyl]amino}-1-piperidinyl)-sulfonyl]

phenyl}benzamide, 4-chloro-N-{3-[(4-{3-[(trifluoromethyl)sulfonyl]anilino}-1-piperidinyl)sulfonyl]phenyl}benzamide, 4-chloro-N-(4-{[3-hexylamino)-1-pyrrolidinyl]sulfonyl}phenyl)benzamide, 4-chloro-N-{4-[(4-{3-[(trifluoromethyl)sulfonyl]anilino}-1-piper-idinyl)sulfonyl]benzyl}benzamide, 4-chloro-N-(4-{[3-({2-[3-(trifluoromethyl)phenyl]ethyl}amino)-1-pyr-rolidinyl]sulfonyl}phenyl)benzamide, N-{3-[(4-anilino-1-piperidinyl)sulfonyl]phenyl}-4-chlorobenzamide, 4-chloro-N-(3-{[4-({2-[3-(trifluoromethyl)phenyl]ethyl}amino)-1-piperidinyl]sulfonyl}phenyl)benzamide, 4-chloro-N-(4-{[3-({2-[3-(trifluoromethyl)phenyl]ethyl}amino)-1-pyr-rolidinyl]sulfonyl}phenyl)benzamide, 4-chloro-N-{3-[(4-{3-[(trifluoromethyl)sulfonyl]anilino}-1-piperidinyl)sulfonyl]benzyl}benzamide, 4-chloro-N-{4-[(4-{3-[(trifluoromethyl)sulfonyl]anilino}-1-piperidinyl)sulfonyl]phenyl}benzamide, 4-chloro-N-{3-[(3-{[4-(trifluoromethyl)benzyl]amino}-1-pyrrolidinyl-)sulfonyl]benzyl}benzamide, 4-chloro-N-(4-{[3-({2-[3-(trifluoromethyl)phenyl]ethyl}amino)-1-pyr-rolidinyl]sulfonyl}benzyl)benzamide, N-(4-{[4-(hexylamino)-1-piperidinyl]sulfonyl}benzyl)-2-hydroxynicotinamide, N-(3-{[4-(hexylamino)-1-piperidinyl]sulfonyl}benzyl)-2-hydro-xynicotinamide, 2-hydroxy-N-{3-[(4-{3-[(trifluoromethyl)sulfonyl]anilino}-1-piperid-inyl)sulfonyl]benzyl}nicotinamide, 2-hydroxy-N-{4-[(4-{3-[(trifluoromethyl)sulfonyl]anilino}-1-piperid-inyl)sulfonyl]benzyl}nicotinamide, and other JNK inhibitors (US Patent Application Publication No. 20080255222); CC105 (B. Bennett et al., Curr. Opin. Pharmacol. (2003) 3:420-25); a compound of Formula I, Formula II, compound 152, compound 153, and other JNK inhibitors (US Patent Application Publication No. 20080033022); a benzazole, a benzothiazole derivative, 1,3-benzothiazol-2-yl(2,6-dimethoxy-4-pyrimidinyl)acetonitrile 1,3-benzothiazol-2-yl(2-{[2-(1H-imidazol-5-yl)ethyl]amino}-4-pyrimidinyl)-acetonitrile 1,3-ben-zothiazol-2-yl[2-(1-piperazinyl)-4-pyrimidinyl]acetonitrile 1,3-benzothiazol-2-yl[2-(4-benzyl-1-piperidinyl)-4-pyrimidinyl]acetonitrile 1,3-benzothiazol-2-yl[2-(4-methyl-1-piperazinyl)-4-pyrimidinyl]acetonitrile 1,3-benzothiazol-2-yl[2-(4-morpholinyl)-4-pyrimidinyl]acetonitrile 1,3-benzothiazol-2-yl[2-(methylamino)-4-pyrimidinyl]acetonitrile 1,3-benzothiazol-2-yl(2-{4-[2-(4-morpholinyl)ethyl]-1-piperazinyl}-4-pyrimidinyl)acetonitrile 1,3-benzothiazol-2-yl{2-[4-(benzyloxy)-1-piperidinyl]-4-pyrimidinyl}acetonitrile 1,3-benzothiazol-2-yl[2-(4-hydroxy-1-piperidinyl)-4-pyrimidinyl]acetonitrile 1,3-benzothiazol-2-yl(2-{[2-(dimethylamino)ethyl]amino}-4-pyrimidinyl)-acetonitrile 1,3-benzothiazol-2-yl[2-(dimethylamino)-4-pyrimidinyl]acetonitrile 1,3-benzothiazol-2-yl{2-[(2-methoxyethyl)amino]-4-pyrimidinyl}acetonitrile 1,3-benzothiazol-2-yl{2-[(2-hydroxyethyl)amino]-4-pyrimidinyl}acetonitrile 1,3-benzothiazol-2-yl[2-(propylamino)-4-pyrimidinyl]acetonitrile 1,3-benzothiazol-2-yl(2-{[3-(1H-imidazol-1-yl)propyl]amino}-4-pyrimidinyl-)acetonitrile 1,3-benzothiazol-2-yl[2-(1-pyrrolidinyl)-4-pyrimidinyl]acetonitrile 1,3-benzothiazol-2-yl{2-[(2-phenylethyl)amino]-4-pyrimidinyl}acetonitrile 1,3-benzothiazol-2-yl(2-{[2-(2-pyridinyl)ethyl]amino}-4-pyrimidinyl)acetonitrile 1,3-benzothiazol-2-yl{2-[(2-pyridinylmethyl)amino]-4-pyrimidinyl}acetonitrile 1,3-benzothiazol-2-yl{2-[4-(1H-1,2,3-benzotriazol-1-yl)-1-piperidinyl]-4-pyrimidinyl}acetonitr-ile 1,3-benzothiazol-2-yl{2-[4-(2-pyrazinyl)-1-piperazinyl]-4-pyrimidinyl}acetonitrile 1,3-benzothiazol-2-yl{2-[4-(2-pyrimidinyl)-1-piperazinyl]-4-pyrimidinyl}acetonitrile 1,3-benzothiazol-2-yl(2-{[2-(3-pyridinyl)ethyl]amino}-4-pyrimidinyl)aceto-nitrile 1,3-benzothiazol-2-yl(5-bromo-2-{[2-(dimethylamino)ethyl]amino}-4-pyrimidinyl)acetonitrile 1,3-benzothiazol-2-yl{2-[(2-morpholin-4-ylethyl)amino]pyrimidin-4-yl}acetonitrile 1,3-benzothiazol-2-yl[2-(4-{3-[(trifluoromethyl)sulfonyl]anilino}piperidin-1-yl)pyrimidin-4-yl]acetonitrile 1,3-ben-zothiazol-2-yl(2-{[3-(2-oxopyrrolidin-1-yl)propyl]amino}pyrimidin-4-yl)acetonitrile 1,3-benzothiazol-2-yl(2-{methyl[3-(methylamino)propyl]amino}pyrimidin-4-yl)acetonitrile 1,3-benzothiazol-2-yl(2-{[3-(4-methylpiperazin-1-yl)propyl]amino}pyrimidin-4-yl)acetonitrile 1,3-benzothiazol-2-yl{2-[(3-morpholin-4-ylpropyl)amino]pyrimidin-4-yl}acetonitrile 1,3-benzothiazol-2-yl(2-{[2-(1-methyl-1H-imidazol-4-yl)ethyl]amino}pyrimi-din-4-yl)acetonitrile 1,3-benzothiazol-2-yl(2-{[2-(1H-indol-3-yl)ethyl]amino}pyrimidin-4-yl)acetonitrile 1,3-benzothiazol-2-yl(2-{[2-(4-hydroxyphenyl)ethyl]amino}pyrimidin-4-yl)acetonitrile tert-butyl ({4-[1,3-ben-zothiazol-2-yl(cyano)methyl]pyrimidin-2-yl}amino)ac-etate{2-[(3-aminopropyl)amino]pyrimidin-4-yl}(1,3-benzothiazol-2-yl)acetonitrile{2-[(2-aminoethyl)amino]pyrimidin-4-yl}(1,3-benzothiazol-2-yl)acetonitr-ile 1,3-benzothiazol-2-yl(2-{[3-(dimethylamino)propyl]amino}pyrimidin-4-yl-)acetonitrile 1,3-benzothiazol-2-yl{2-[(2-piperidin-1-ylethyl)amino]pyrimidin-4-yl}acetonitrile 1,3-benzothiazol-2-yl(2-{[2-(1-methyl-1H-imidazol-5-yl)ethyl]amino}pyrimi-din-4-yl)acetonitrile 1,3-benzothiazol-2-yl[2-(benzylamino)pyrimidin-4-yl]acetonitrile isopropyl 3-({4-[1,3-benzothiazol-2-yl(cyano)methyl]pyrimidin-2-yl}amino)-propanoate 1,3-benzothiazol-2-yl{2-[(3-hydroxypropyl)amino]pyrimidin-4-yl}acetonitrile 1,3-benzothiazol-2-yl{2-[(pyridin-3-ylmethyl)amino]pyrimidin-4-yl}acetonitrile 1,3-benzothiazol-2-yl{2-[(pyridin-4-ylmethyl)amino]pyrimidin-4-yl}acetonitrile tert-butyl 4-[2-({4-[1,3-benzothiazol-2-yl(cyano)methyl]pyrimidin-2-yl}amino)-ethyl]-phenylcarbamate (2-{[2-(4-aminophenyl)ethyl]amino}pyrimidin-4-yl)(1,3-benzothiazol-2-yl)acetonitrile 1,3-benzothiazol-2-yl(2-{[2-(3,4-dimethoxyphenyl)ethyl]amino}pyrimidin-4-yl)acetonitrile 1,3-benzothiazol-2-yl(2-{[2-(3-methoxyphenyl)ethyl]amino}pyrimidin-4-yl)aceto-nitrile 1,3-benzothiazol-2-yl(2-{[2-(2-fluorophenyl)ethyl]amino}pyrimidin-4-yl)acetonitrile 1,3-benzothiazol-2-yl[2-({2-[3-(trifluoromethyl)phenyl]ethyl}am-ino)pyrimidin-4-yl]acetonitrile 1,3-benzothiazol-2-yl{2-[(2-hydroxy-2-phenylethyl)amino]pyrimidin-4-yl}acetonitrile 1,3-benzothiazol-2-yl{2-[(2-{[3-(trifluoromethyl)pyridin-2-yl]amino}ethyl)amino]-pyrimidin-4-yl}acetonitrile 1,3-benzothiazol-2-yl(2-{[2-(3-chlorophenyl)ethyl]amino}pyrimidin-4-yl)acetonitrile 1,3-benzothiazol-2-yl(2-{[2-(3,4-dichlorophenyl)ethyl]amino}pyr-imidin-4-yl)acetonitrile 1,3-benzothiazol-2-yl(2-{[2-(4-methoxyphenyl)ethyl]amino}pyrimidin-4-yl)acetonitrile 1,3-benzothiazol-2-yl(2-{[2-(4-methylphenyl)ethyl]amino}pyrimidin-4-yl)acetonitrile 1,3-benzothiazol-2-yl(2-{[2-(3-fluorophenyl)ethyl]amino}pyrimidin-4-yl)acetonitrile 1,3-benzothiazol-2-yl(2-{[2-(4-phenoxyphenyl)ethyl]amino}pyrimidin-4-yl)acetonitrile 1,3-benzothiazol-2-yl(2-{[2-(2-phenoxyphenyl)ethyl]amino}pyrimidin-4-yl)acetonitrile 1,3-benzothiazol-2-yl(2-{[2-(4-bromophenyl)ethyl]amino}pyrimidin-4-yl)acetonitrile 1,3-benzothiazol-2-yl(2-{[2-(4-fluorophenyl)ethyl]amino}pyrimidin-4-yl)acetonitrile 1,3-benzothiazol-2-yl{2-[(2-[1,1'-biphenyl]-4-ylethyl)amino]pyrimidin-4-yl}acetonitrile 1,3-benzothiazol-2-yl{2-[(2-{4-[hydroxy(oxido)amino]phenyl}ethyl)amino]pyrimidin-4-yl}acetonitrile 1,3-benzothiazol-2-yl(2-{[2-(1H-1,2,4-triazol-1-yl)ethyl]amino}pyrimi-din-4-yl)acetonitrile 1,3-benzothiazol-2-yl(2-{[3-(1H-pyrazol-1-yl)propyl]

amino}pyrimidin-4-yl)-acetonitrile 4-[2-({4-[1,3-benzothiazol-2-yl(cyano)methyl]pyrimidin-2-yl}amino) ethyl]benzenesulfonamide{2-[(2-pyridin-3-ylethyl)amino] pyrimidin-4-yl}[5-(trifluoromethyl)-1,3-be-nzothiazol-2-yl]acetonitrile 1,3-benzothiazol-2-yl{2-[(1H-tetraazol-5-ylmethyl)amino]pyrimidin-4-yl}acetonitrile 1,3-benzothiazol-2-yl[2-(benzyloxy)pyrimidin-4-yl]acetonitrile 1,3-benzothiazol-2-yl{2-[(4-pyridin-3-ylbenzyl)oxy]pyrimidin-4-yl}acetonitrile 1,3-benzothiazol-2-yl[2-(pyridin-4-ylmethoxy)pyrimidin-4-yl]acetonitrile 1,3-benzothiazol-2-yl[2-(pyridin-2-ylmethoxy)pyrimidin-4-yl]acetonitrile 1,3-benzothiazol-2-yl[2-(3-pyridin-2-ylpropoxy)pyrimidin-4-yl]acetonitrile 1,3-benzothiazol-2-yl{2-[(4-methoxybenzyl)oxy]pyrimidin-4-yl}acetonitrile 1,3-benzothiazol-2-yl[2-(pyridin-3-ylmethoxy)pyrimidin-4-yl]acetonitrile 1,3-benzothiazol-2-yl{2-[2-(4-methoxyphenyl)ethoxy] pyrimidin-4-yl}acetonitrile 1,3-benzothiazol-2-yl[2-([1,1'-biphenyl]-3-ylmethoxy)pyrimidin-4-yl]aceto-nitrile 1,3-benzothiazol-2-yl{2-[(3,4,5-trimethoxybenzyl)oxy] pyrimidin-4-yl}acetonitrile 1,3-benzothiazol-2-yl{2-[(3,4-dichlorobenzyl)oxy]pyrimidin-4-yl}acetonitrile 1,3-benzothiazol-2-yl[2-({3-[(dimethylamino)methyl] benzyl}oxy)pyrimidin-4-yl]acetonitrile 1,3-benzothiazol-2-yl {2-[(1-oxidopyridin-3-yl)methoxy]pyrimidin-4-yl}acetonitrile 1,3-benzothiazol-2-yl(2-{[4-(morpholin-4-ylmethyl)benzyl]oxy}pyrimidin-4-yl)acetonitrile 1,3-benzothiazol-2-yl{2-[(4-pyridin-2-ylbenzyl)oxy]pyrimidin-4-yl}acetonitrile 1,3-benzothiazol-2-yl(2-{[4-(piperidin-1-ylmethyl)benzyl]oxy}pyrimidin-4-yl)acetonitrile 1,3-benzothiazol-2-yl[2-(4-methoxyphenoxy)pyrimidin-4-yl] acetonitrile 1,3-benzothiazol-2-yl[2-(4-butoxyphenoxy) pyrimidin-4-yl]acetonitrile {2-[4-(4-acetylpiperazin-1-yl) phenoxy]pyrimidin-4-yl}(1,3-benzothiazol-2-yl)acetonitrile [2-(4-methoxyphenoxy)pyrimidin-4-yl][5-(trifluoromethyl)-1,3-benzothiazol-2-yl]acetonitrile N-[2-({4-[1,3-benzothiazol-2-yl(cyano)methyl]pyrimidin-2-yl}amino)ethyl]—4-chlorobenzamide 1,3-benzothiazol-2-yl (2-methoxy-4-pyrimidinyl)acetonitrile 1,3-benzothiazol-2-yl[2-({4-[(4-methylpiperazin-1-yl)methyl]benzyl}oxy) pyrimidin-4-yl]acetonitrile 1,3-benzothiazol-2-yl[2-({4-[(4-benzyl-piperazin-1-yl)methyl]-benzyl}oxy)-pyrimidin-4-yl] acetonitrile 1,3-benzothiazol-2-yl(2-{[4-(piperazin-1-ylmethyl)benzyl]oxy}pyrimidin-4-yl)acetonitrile 1,3-benzothiazol-2-yl[2-({4-[(4-formylpiperazin-1-yl)methyl] benzyl}oxy)pyrimidin-4-yl]acetonitrile[2-({4-[(4-acetylpiperazin-1-yl)methyl]benzyl}oxy)pyrimidin-4-yl](1,3-benzothiazol-2-yl)acetonitrile(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile 4-(4-{4-[(3H-Benzothiazol-2-ylidene)-cyano-methyl]-pyrimidin-2-yloxymethyl}-benzyl)-piperazine-1-carboxylic acid methyl ester 2-[4-(4-{4-[(3H-Benzothiazol-2-ylidene)-cyano-methyl]-pyrimidin-2-yloxyme-thyl}-benzyl)-piperazin-1-yl]-acetamide(2-{4-[4-(2-Amino-acetyl)-piperazin-1-ylmethyl]-benzyloxy}-pyrimidin-4-yl-)-(3H-benzothiazol-2-ylidene)-acetonitrile[4-(4-{4-[(3H-Benzothiazol-2-ylidene)-cyano-methyl]-pyrimidin-2-yloxymeth-yl}-benzyl)-piperazin-1-yl]-acetic acid methyl ester (3H-Benzothiazol-2-ylidene)-(2-{4-[4-(2-methoxy-ethyl)-piperazin-1-ylmeth-yl]-benzyloxy}-pyrimidin-4-yl)-acetonitrile 4-(4-{4-[(3H-Benzothiazol-2-ylidene)-cyano-methyl]-pyrimidin-2-yloxymethyl}-benzyl)-piperazine-1-carboxylic acid dimethylamide (3H-Benzothiazol-2-ylidene)-{2-[4-(4-ethyl-piperazin-1-ylmethyl)-benzyloxy]-pyrimidin-4-yl}-acetonitrile (3H-Benzothiazol-2-ylidene)-(2-{4-[4-(2-hydroxy-ethyl)-piperazin-1-ylmeth-yl]-benzyloxy}-pyrimidin-4-yl)-acetonitrile, and other JNK inhibitors (US Patent Application Publication No. 20080039377); Compounds 1 to 142, and other dihydroquinone and dihydronaphthridine inhibitors of JNK, (US Patent Application Publication No. 20080287458); AS601245 [1,3-benzothiazol-2-yl(2-[[2-(3-pyridinyl)ethyl] amino]-4 pyrimidinyl)acetonitrile] (J Pharmacol Exp Ther 2004; 310:25-32); and JNK inhibitor III (J Biol Chem 2003; 278:40213-23).

In addition to the possible involvement of ASK1 and JNK, it is also contemplated that extracellular signal-regulated kinase (ERK), Akt, and signalling pathways related thereto are involved in diabetic embryopathy. ERK, Akt, and signalling pathways related thereto are involved in pathways that can act to prevent cells from undergoing apoptotic cell death, which is an antagonistic effect when compared to JNK and ASK1, as described above. Considering this, one aspect of the present invention is the discovery and use of an agent that modulates (e.g., increases) the activity of ERK (including, for example, ERK1 and ERK2) and/or Akt to treat a diabetic embryopathy.

In certain aspects of the invention drawn to an agent that modulates the activity of ERK, modulation of ERK comprises increasing the activity of ERK. In further certain aspects, modulation of ERK includes increasing the activity of ERK. In other further certain aspects, the agent that modulates the activity of ERK is effective for treating a diabetic embryopathy. In certain aspects, an ERK modulator includes, for example, epidermal growth factor (EGF); an agonist anti-ERK antibody; biliverdin reductase (Lerner-Marmarosh et al., Proc Natl Acad Sci USA. 2008 May 13; 105(19):6870-5); urea (Yang et al., Am J Physiol Renal Physiol 277: F176-F185, 1999); phorbol myristate acetate (PMA; Kim et al., BMC Cancer 2009, 9:27); and FGF-2 (Kalluri et al., European Journal of Neuroscience: Volume 25(4) February 2007p 1041-1048).

In certain aspects of the invention drawn to an agent that modulates the activity of Akt, modulation of Akt comprises increasing the activity of Akt. In further certain aspects, modulation of Akt consists of increasing the activity of Akt. In other further certain aspects, the agent that modulates the activity of Akt is effective for treating a diabetic embryopathy. In certain aspects, an Akt modulator includes, for example, Ro 31-8220 (Hemström et al., Int J Cancer. 2006 Sep. 1; 119(5):1028-38); IGF-1 (Hsu et al., Endocrine-Related Cancer 14 (3) 655-667); bis(1-oxy-2-pyridinethiolato) oxovanadium (IV) and other vanadium compounds (Bhuiyan et al., Expert Opinion on Therapeutic Targets October 2008, Vol. 12, No. 10, Pages 1217-1227); pervanadate and platelet-derived growth factor (Bozinovski et al., Analytical Biochemistry (2002) 305, 32-39); L-alpha-Phosphatidyl inositol-3,4, 5-tris phosphate (Tang et al., Invest. Opthalmol. Vis. Sci. 43: E-Abstract 772); carboxy-terminal modulator protein (CTMP; Franke T. F., Am J Physiol Cell Physiol (Oct. 3, 2007). doi:10.1152/ajpcell.00451.2007); stem cell factor (SCF) and heregulin (Hines et al., Breast Cancer Research and Treatment 58: 1-10, 1999); insulin (Cenni et al., J. Proteome Res., 2008, 7 (11), 4727-4735); brain derived neurotrophic factor (BDNF; Nakazawa et al., Invest Opthalmol Vis Sci 2004; 45: E-Abstract 872); hepatocyte growth factor (Elghazi et al., Diabetes, Obesity and Metabolism, 9 (Suppl. 2), 2007, 147-157); 2-(2,2,4,6,7-pentamethyl-3-phenyl-2,3-dihydro-1-benzof-uran-5-yl)isoindoline, 5,6-dichloro-2-(2, 2,4,6,7-pentamethyl-3-phenyl-2,3-dih-ydro-1-benzofuran-5-yl)isoindoline, 5,6-dimethoxy-2-(2,2,4,6,7-pentamethyl-3-phenyl-2,3-di-hydro-1-benzofuran-5-yl)isoindoline, 2-[2, 2,4,6,7-pentamethyl-3-(4-methylphenyl)-2,3-dihydro-1-benzofuran-5-yl]isoindoline, 5,6-dichloro-2-[2,2,4,6,7- pentamethyl-3-(4-methylpheny-1)-2,3-dihydro-1-benzofuran-5-yl]isoindoline, 5,6-dimethoxy-2-[2,2,4,6,7-pentamethyl-3-(4-methylphen-yl)-2,3-dihydro-1-benzofuran-5-yl]isoindoline, 2-[3-(4-fluorophenyl)-2,2,4,6,7-pentamethyl-2,3-dihydro-1-benzofuran-5-yl]isoindoline, 5,6-dichloro-2-[3-(4-fluorophenyl)-2,2,4,6,7-pentamethyl-2,3-dihydro-1-benzofuran-5-yl]isoindoline, 2-[3-(4-isopropylphenyl)-2,2,4,6,7-pentamethyl-2,3-dihydro-1-benzofuran-5-yl]isoindoline, 5,6-dichloro-2-[3-(4-isopropylphenyl)-2,2,4,6,7-penta-methyl-2,3-dihydro-1-benzofuran-5-yl] isoindoline, 5,6-dimethoxy-2-[3-(4-isopropylphenyl)-2,2,4,6,7-pentamethyl-2,3-dihydro-1-benzofuran-5-yl] isoindoline, 6-[3-(4-isopropylphenyl)-2,2,4,6,7-pentamethyl-2,3-di-hydro-1-benzofuran-5-yl]-6,7-dihydro-5H-[1,3]dioxolo[4,5-f]isoindole, 2-[3-(4-isopropylphenyl)-2,4,6,7-tetramethyl-1-benzofuran-5-yl]isoindoline, 6-[2,2,4,6,7-pentamethyl-3-(4-methylphenyl)-2,3-dihydro-1-benzofuran-5-yl]-6H-[1,3]dioxolo[4,5-f]isoindole, 2-[2,2,4,6,7-pentamethyl-2,3-dihydro-1-benzofuran-5-yl] isoindoline, 6-(2,2,4,6,7-pentamethyl-3-phenyl-2,3-dihydro-1-benzo-furan-5-yl)-6,7-dihydro-5H-[1,3]dioxolo[4,5-f]isoindole, (+)-5,6-dimethoxy-2-[2,2,4,6,7-pentamethyl-3-(4-methylphenyl)-2,3-dihydro-1-benzofuran-5-yl]isoindoline, (−)-5,6-dimethoxy-2-[2,2,4,6,7-pentamethyl-3-(4-methyl-lphenyl)-2,3-dihydro-1-benzofuran-5-yl]isoindoline, (+)-5,6-dimethoxy-2-[2,2,4,6,7-pentamethyl-3-(4-methyl-lphenyl)-2,3-dihydro-1-benzofuran-5-yl]isoindoline hydrochloride, (−)-5,6-dimethoxy-2-[2,2,4,6,7-pentamethyl-3-(4-methylphenyl)-2,3-dihydro-1-benzofuran-5-yl]isoindoline hydrochloride, (+)-5,6-dimethoxy-2-[2,2,4,6,7-pentamethyl-3-(4-methyl-lphenyl)-2,3-dihydro-1-benzofuran-5-yl]isoindoline hydrobromide, (−)-5,6-dimethoxy-2-[2,2,4,6,7-pentamethyl-3-(4-methyl-lphenyl)-2,3-dihydro-1-benzofuran-5-yl]isoindoline hydrobromide, 5,6-dimethoxy-2-[2,2,4,6,7-pentamethyl-3-(4-methylphe-nyl)-2,3-dihydro-1-benzofuran-5-yl]-2H-isoindole, and other compounds of Formula I (US Patent Application Publication No. 20050148650); and an agonist anti-Akt antibody.

In certain aspects of the invention drawn to a diabetic embryopathy or treating a diabetic embryopathy, a diabetic embryopathy includes, for example, a central nervous system (CNS) abnormality, anomaly, or malformation (including, for example, neural tube defect, nencephaly, holoprosencephaly, hydrocephalus, absent corpus callosum, Arnold-Chiari anomaly, schizencephaly, microcephaly, macrocephaly, agenesis of olfactory tracts, intracranial lipoma, facial nerve palsy, calcified falx cerebi, abnormal undergrowth or overgrowth of the brain, postnatal developmental delay); a cardiovascular abnormality, anomaly, or malformation (including, for example, complex transposition of the great vessels, single ventricle or atria, hypoplastic left heart, tricuspid atresia, tetralogy of fallot, ventricular septal defect, atrial septal defect, double outflow right ventricle, pulmonary atresia, coarctation of the aorta, subaortic stenosis, right aortic arch, tricuspid regurgitation, cleft mitral valve, symmetric hypertrophy of interventricular septum, hypertrophic cardiomyopathy); a gastrointestinal abnormality, anomaly, or malformation (including, for example, situs inversus, pyloric stenosis, duodenal atresia, small bowel atresias, small left colon (microcolon) syndrome, rectal atresia, anal atresia (imperforate anus), meckel diverticulum, diaphragmatic hernia, omphalo-enteric cyst/fistula); a genitourinary abnormality, anomaly, or malformation (including, for example, renal agenesis, cystic kidneys, ectopic kidney, hydronephrosis, ureteral duplication, ureterocele, ambiguous genitalia, hypospadias, micropenis, cryptorchidism, uterine agenesis, hypoplastic vagina); a skeletal abnormality, anomaly, or malformation (including, for example, hand anomalies or limb reduction defects (e.g., radial clubbing, bifid thumbs, hypoplastic/absent thumb, radial hypoplasia), polysyndactyl), contractures, costovertebral anomalies (e.g., fused cervical vertebrae, hemivertebrae, torticolis, bifid/fused ribs), hip dislocation, femoral hypoplasia, caudal regression (e.g., agenesis of sacrum and lumbar spine, hypoplasia of the lower extremities, phocomelia), craniosynostosis); a facial abnormality, anomaly, or malformation (including, for example, hemifacial microsomia (oculoauriculovertebral anomalies), macrostomia/lateral facial cleft, cleft lip/palate, micrognathia, branchial cleft cyst, frontonasal dysplasia, choanal atresia, short nose, nasal milia, fat pad across nose, facial skin tags); an eye abnormality, anomaly, or malformation (including, for example, lens opacity, cataracts, microophthalmia/optic nerve hypoplasia, colobomas of iris or chorioretina, anterior chamber dysgenesis, epibulbar dermoid/oculolipoma, laterally displaced inner canthi, tear duct obstruction); an ear abnormality, anomaly or malformation (including, for example, microtia, sensorineural/conductive hearing loss, preauricular tags, anotia, atretic ear canal); or a skin abnormality, anomaly, or malformation (including, for example, aplasia cutis, cutaneous vascular dysplasia).

In certain aspects of the invention drawn to a diabetic embryopathy or treating a diabetic embryopathy, an agent described herein can be used in combination with another agent described herein or another method of treating a diabetic embryopathy. Another method of treating a diabetic embryopathy, includes for example, a multi-nutrient supplement regimen (U.S. Pat. No. 7,438,933).

Thus, example methods of treating a diabetic embryopathy provided herein may include administering to a mammal in need thereof at least one agent that modulates the activity of at least one polypeptide selected from the group consisting of ASK, JNK, ERK and Akt; and at least one other agent. Example methods of treating a diabetic embryopathy also include administering to a mammal in need thereof at least one agent that modulates the activity of at least one polypeptide selected from the group consisting of ASK, JNK, ERK and Akt; and providing or administering a multi-nutrient supplement regimen to the mammal.

In certain aspects of the invention drawn to administering an agent of the invention, routes of administration and dosage are known, or can be determined, by one of ordinary skill in the art. Described below are, for illustrative purposes only, routes of administration and dosages. The illustration specifically teaches administration of an agent that modulates JNK. However, one of ordinary skill in the art would appreciate that the below description and teachings not only apply to an agent that modulates JNK, but also to any other agent of the invention that modulates the activity of, for example, ASK1, ERK, and Akt.

Methods of administering an agent that modulates JNK and optionally a second agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the agent that modulates JNK and optionally a second agent are administered intramuscularly, intravenously, or subcutaneously. The agent that modulates JNK and optionally a second agent can also be administered by infusion or bolus injection and can be administered together with another agent or method of treating a diabetic embryopathy. Administration can be local or systemic. The agent that modulates JNK and optionally a second agent and their physiologically acceptable salts and solvates can also be administered by inhalation or insufflation (either through the mouth or the nose). In one embodiment, local or systemic parenteral administration is used.

In specific embodiments, it can be desirable to administer the agent that modulates JNK locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the agent that modulates JNK can be formulated as a suppository, with traditional binders and vehicles such as triglycerides.

In another embodiment, the agent that modulates JNK can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the agent that modulates JNK can be delivered in a controlled release system. In one embodiment, a pump can be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J. Macromol. Sci. Rev. Macromol. Chem. 23:61; see also Levy et al., 1985, Science 228:190; During et al., 1989, Ann Neurol. 25:351; Howard et al., 1989, J. Neurosurg. 71:105). In yet another embodiment, a controlled-release system can be placed in proximity of the target of the agent that modulates JNK, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science (1990) 249:1527-1533) can be used.

The amount of the agent that modulates JNK that is effective in the treatment, prevention or management of a diabetic embryopathy can be determined by standard research techniques. For example, the dosage of the agent that modulates JNK that will be effective in the treatment a diabetic embryopathy can be determined by administering the agent that modulates JNK in an animal model (e.g., the animal models known to those skilled in the art). In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the patient's body mass, the patient's immune status and other factors known by the skilled artisan.

The precise dose to be employed in the formulation will also depend on the route of administration and the seriousness and nature of the diabetic embryopathy, which should be decided according to the judgment of the practitioner and each patient's circumstances. Effective doses can be extrapolated from dose-response curves derived from in vitro or animal model test systems.

The dose of agent that modulates JNK to be administered to a patient, such as a human, is rather widely variable and can be subject to independent judgment. It is often practical to administer the daily dose of an agent that modulates JNK at various hours of the day. However, in any given case, the amount of an agent that modulates JNK administered will depend on such factors as the solubility of the active component, the formulation used, patient condition (such as weight), and/or the route of administration.

The general range of effective amounts of an agent that modulates JNK alone or in combination with a second agent are from about 0.001 mg/day to about 1000 mg/day, from about 0.001 mg/day to 750 mg/day, from about 0.001 mg/day to 500 mg/day, 0.001 mg/day to 250 mg/day, from about 0.001 mg/day to 100 mg/day, from about 0.001 mg/day to 75 mg/day from about 0.001 mg/day to 50 mg/day from about 0.001 mg/day to 25 mg/day, from about 0.001 mg/day to 10 mg/day, from about 0.001 mg/day to 1 mg/day. Of course, it is often practical to administer the daily dose of an agent of the invention in portions, at various hours of the day. However, in any given case, the amount of an agent of the invention administered will depend on such factors as the solubility of the active component, the formulation used, subject condition (such as weight), and/or the route of administration.

While the invention has been described with reference to certain particular embodiments, those skilled in the art will appreciate that various modifications may be made without departing from the spirit and scope of the invention. The scope of the appended claims is not to be limited to the specific embodiments described.

EXAMPLES

Example 1

Diabetic Model

Maternal Diabetic Model

In order to study maternal diabetes-associated embryopathy, an animal model has been generated in which, for example, streptozotocin (STZ) is used to induce diabetes in female rats. Glucose levels are controlled by reintroducing insulin in the form of a removable, implanted pellet. This type of animal model, which has been widely used, has a number of advantages over spontaneous diabetic animal models. First, glucose levels can be controlled by changing the amount of insulin introduced. Second, diabetes can be induced at desired developmental stages by removing the insulin pellet at the appropriate time. Similar models have also been used by other researchers in this field with similar reported outcomes.

To induce diabetes, 8-week-old Sprague-Dawley female rats are injected with 65 mg/kg of streptozotocin via the tail vein. Blood glucose levels are monitored daily (by tail vein puncture using a lancet) using a PRESTIGE SMART blood glucose meter (Home Diagnostics, Fort Lauderdale, Fla.). Once a level of hyperglycemia indicative of diabetes (>250 mg/dl) is achieved, a sustained-release insulin pellet is inserted subcutaneously. When glucose levels are restored to normal (80-150 mg/dl) and are stable for at least three continuous days, matings can be set up with male rats of the same strain. Day zero of pregnancy is established by identifying spermatozoa in vaginal smears. At designated developmental stages, insulin pellets are withdrawn to generate hyperglycemia in the pregnant rats. A group of control rats continue to receive insulin during the course of the experiment. Glucose levels and maternal weight are continuously monitored during the pregnancy. Since it has already been shown that there is no difference in embryonic development between streptozotocin/insulin-treated and non-streptozotocin-treated animals, the streptozotocin/insulin-treated groups are used as an equivalent of non-diabetic control. At the end of the experiment, rats are euthanized and embryos dissected out of the uterus for examination and analysis. At least four pregnant rats are included in each group, from which 40-60 embryos can be obtained for examination. For each type of study, replicate experiments are carried out.

The embryos are characterized morphologically in terms of growth and structural abnormality. Embryonic growth can be determined by the size of embryo, including head/rump length and body weight. Structural abnormality includes agenesis, hypoplasia, incomplete neural tube closure, microcephaly, cardiac defects, and incorrect body curvature. Specimens are also sectioned and examined at the histological level. Attention is given to the organs that have been documented to be negatively affected by hyperglycemia.

Whole Embryo Culture

While an in vivo diabetic animal model provides important information about morphological and molecular changes during development, it may be difficult to treat the embryos in utero with an agent of the invention. To delineate the roles of factors in hyperglycemia-associated embryonic malformation, a whole embryo culture system can be used in which the embryos are exposed to different glucose concentrations. It has been validated that this type of whole embryo culture mimics in vivo development of an embryo under maternal diabetes. In this culture system, the embryos are treated with an agent of the invention that modulates the activity of specific factors and components of signaling pathways. A whole-embryo culture system, modified from the roller bottle system, has been routinely used. This culture system allows embryos from stages E8.5 to E12.5 to develop normally in vitro for 48-72 hours with controlled oxygen levels that mimic conditions in utero. Therefore, it is a useful, reliable, and manipulatable system for studying early embryogenesis and organogenesis.

Embryos at different stages of gestation are dissected out of uterus with the yolk sacs intact. The embryos are then cultured in rat serum (five embryos/bottle) at 38° C. with rotation at 30 revolutions per minute. Glucose is added to the cultures to generate euglycemic (80-150 mg/dl) and various hyperglycemic (300 mg/dl, 600 mg/dl, 950 mg/dl) conditions. Embryos are treated with an agent of the invention under hyperglycemic and control conditions for 24-72 hours. At the end of culture, embryos are collected for morphological and histological examination and biochemical analyses. At least 10 embryos are included in each group.

Cell Culture

The maternal diabetic animal model and embryo culture described above provide useful systems for investigating the effects of hyperglycemia on embryogenesis and the mechanisms by which hyperglycemia causes developmental malformations. To delineate the molecular mechanisms in depth, a cell culture system is used to test various hypotheses at cellular and molecular levels. For example, NIH 3T3 fibroblasts, which are derived from murine embryonic cells, are suitable for delineating the molecular mechanisms of hyperglycemia-induced embryopathy. 3T3 cells can be purchased from American Type Culture Collection (ATCC, Manassas, Va.) and maintained in conditions recommended by ATCC. For each experiment, cells are plated and grown to desired density before treatment. After treatment, cells are harvested at different time points for cellular and molecular analyses. Primary embryonic cells from the tissues affected by hyperglycemia can also be examined to investigate if there are cell type-specific effects.

Example 2

Maternal Diabetes Correlates with Increased Embryo Malformation Rates

To investigate the effects of maternal hyperglycemia on embryonic malformations, the inventors employed a rat model that induces diabetes by streptozotocin (STZ), as described above. Subcutaneously implanted insulin pellets maintained euglycemia at the time of mating. On day 4 of pregnancy, the insulin pellets were removed, and the developing embryos were exposed to hyperglycemia during organogenesis (days 9-12). To maintain a euglycemic control, insulin pellets were retained in the body during the entire experimental course. On day 12, rats were euthanized, embryos were dissected out of the uteri for examination, and each embryo's yolk sac was collected for biochemical and molecular analyses.

After removal from the dams, embryos were examined under a dissecting microscope and assessed for morphological malformations in a number of categories to determine the effects of maternal hyperglycemia. Embryos were classified as normal if examination revealed correct body flexure, both anterior and posterior neural pole closure, and grossly normal heart. Embryos were classified as malformed if they showed evidence of neural tube defects (NTDs) or other malformations, including cardiac abnormalities, incorrect body curvature, reverse tail flexion, and microcephaly. The results demonstrate that malformation rates (as assessed by morphological defects) in the diabetic rats are more than 6-fold higher than that in non-diabetic control rats or in euglycemic control rats whose insulin pellets were left in place.

Example 3

Hyperglycemia Induces Embryonic Malformations In Vitro

To further demonstrate that hyperglycemia plays a role in increased malformation rates in the embryos, an in vitro embryo culture model was used in which experimental conditions can be precisely controlled. Embryos at E10 were cultured in control medium consisting of 80% (vol/vol) rat serum in which glucose concentration was 150 mg/dl. Embryos were treated with various concentrations of glucose. After 24 hours of culture, control embryos developed normally into E11-like embryos. However, embryos treated with high concentrations of glucose (300 mg/dl, 600 mg/dl, and 950 mg/dl) exhibited abnormalities of the neural tube, heart, pericardium, and body flexion. These phenotypes are similar to those seen in in vivo models of diabetes, indicating that hyperglycemia directly affects embryonic development in vitro in a manner corresponding to that seen in vivo. These experiments demonstrate that high concentrations of glucose have teratogenic effects on embryos, and whole embryo culture provides a powerful experimental system to test various aspects of hyperglycemic effects on embryonic development.

Example 4

Maternal Diabetes Results in Alterations of Stress-Activated MAPKS

Experiments were conducted to study potential changes in the levels of phosphorylated MAPKs resulting from maternal hyperglycemia. While there are many MAPKs, the following studies focus on two families, the ERKs (ERK-1 and -2) and JNKs (JNK-1 and -2), for two primary reasons. First, several lines of evidence indicate that ERK and JNK are involved in cell survival and cell death. Second, these factors have also been associated with diabetic complications and with development of embryos and cells under hyperglycemic conditions. The roles of ERK-1 and -2 and JNK-1 and -2 in diabetic embryopathy, however, have not been extensively studied.

Figure 2:
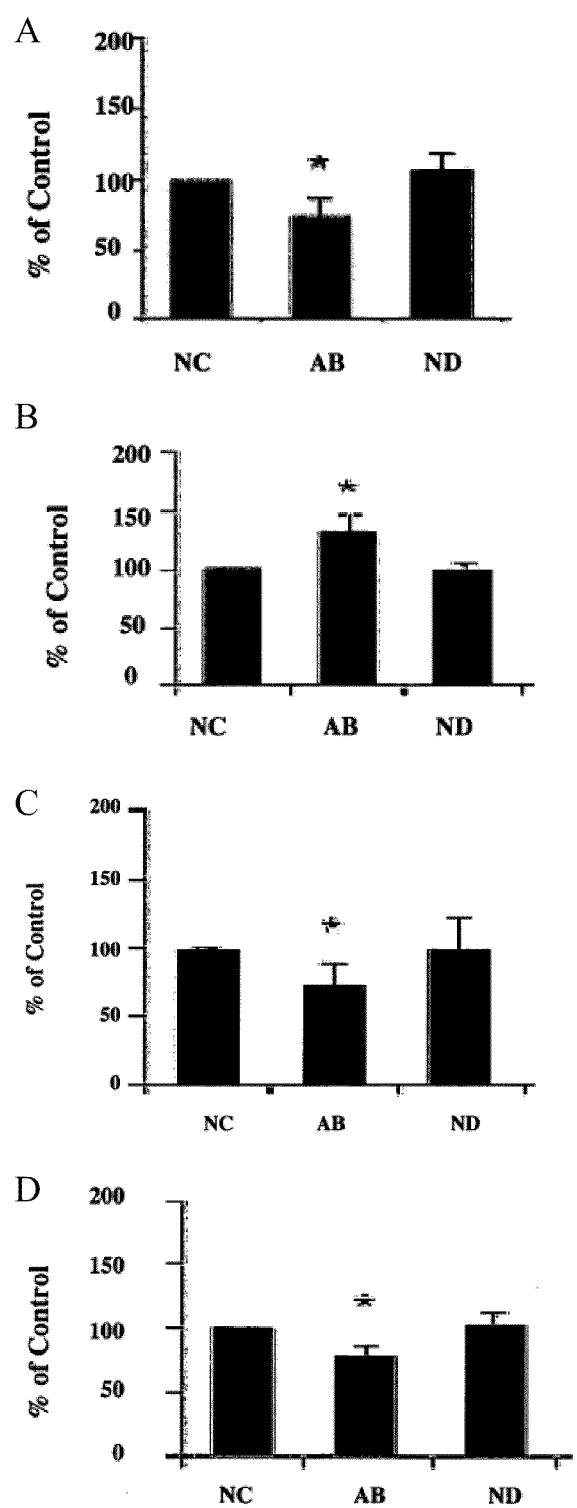
FIG. 2A-D. Densitometrical analysis of changes of ERK1/2, JNK1/2, Raf-1 and Akt are shown in FIGS. 2A, 2B, 2C, and 2D, respectively. NC: non-diabetic control; AB: abnormal embryo from diabetic; and ND: normal embryo from diabetic.

The active forms of ERK and JNK are phosphorylated, so their activation in yolk sac tissues is assessed by Western blot detection of the corresponding phosphoproteins. The levels of phosphorylated Raf-1 which activates ERKs and Akt which is an antiapototic protein were also assessed by western blot. Yolk sac tissues were isolated, protein was extracted and analyzed using Western blotting with antibodies specific for phosphorylated ERK-1 and -2 (p-ERK1/2), JNK-1 and -2 (p-JNK1/2), RAF-1 and Akt (FIG. 1). Levels of p-ERK1/2, Raf-1 and Akt were dramatically decreased in yolk sac cells of malformed embryos as compared to those of normal embryos from diabetic or non-diabetic mothers (control groups) (FIGS. 2A, 2C and 2D). In contrast, p-JNK1/2 was significantly increased in the yolk sac cells of malformed embryos from diabetic rats as compared to those from the two control groups (FIG. 2B). These findings suggest that maternal diabetes alters activation of ERK and JNK kinases and supports that hyperglycemia-induced diabetic embryopathies are associated with changes in stress-activated MAPK signaling pathways.

Example 5

Maternal Diabetes Results in Alterations of ASK1

Figure 3:
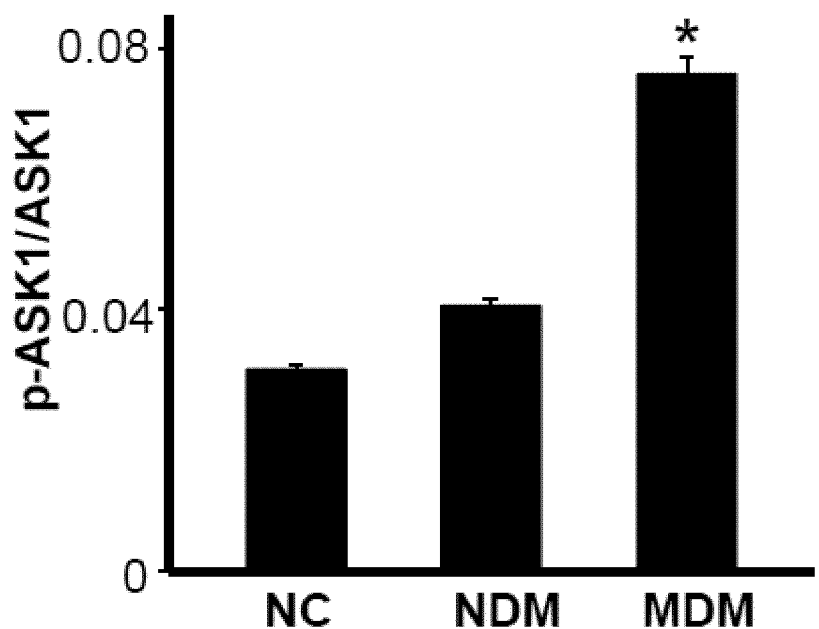
FIG. 3. Demonstrates that hyperglycemia induces changes in phosphorylated ASK1. NC: normal embryo from non-diabetic; NDM: normal embryo from diabetic; MDM: malformed embryo from diabetic.

To determine the role of ASK1 in diabetic embryopathy, phopho-ASK1 (pASK1) levels were evaluated in the neural tube of embryos taken from experiment subjects. The neural tube was dissected from normally developed E11 embryos from non-diabetic mice (NC) or diabetic mice (NDM), and from malformed E11 embryos from diabetic mice (MDM). pASK1 levels were increased in neural tubes of malformed embryos from MDM mice compared to levels in neural tubes of NC and NDM mice (FIG. 3). Increased levels of pASK1 correlated with increased levels of pJNK1/2 in MDM groups compared to those in NC and NDM groups, suggesting that ASK1 mediates hyperglycemia-induced JNK1/2 activation.

Figure 4:
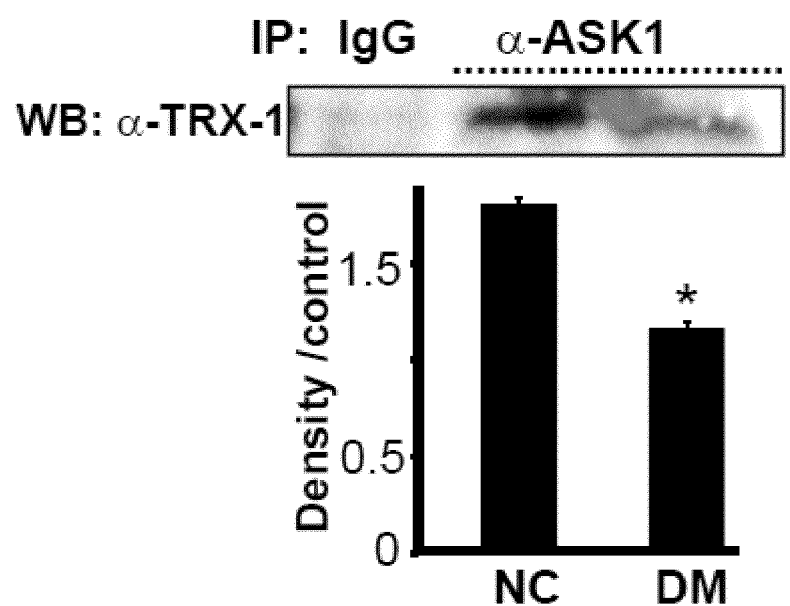
FIG. 4. Demonstrates that hyperglycemia induces ASK1-TRX-1 complexes. NC: normal embryo from non-diabetic; NDM: normal embryo from diabetic; MDM: malformed embryo from diabetic.

To further confirm that maternal hyperglycemia activates ASK1, immunoprecipitation was used to determine the interaction between ASK1 and TRX-1. TRX-1 is an endogenous suppressor of ASK1 and is constantly associated with non-active ASK1 at normal physiological states. Upon oxidative stress, ROS oxidizes TRX-1 which subsequently dissociates from ASK1 leading to ASK1 phosphorylation. ASK1 protein complexes were immunoprecipitated in lysates of E9 embryos from NC and DM mice using a specific ASK1 antibody. Subsequently, levels of TRX1 were determined in ASK1 immunoprecipitates by immunoblotting. TRX-1 levels in DM ASK1 immunoprecipitates were significantly lower than those in NC ASK1 immunoprecipitates, demonstrating that maternal hyperglycemia induces disassociation of ASK1-TRX-1 complexes, leading to ASK1 activation (FIG. 4). E9 embryos were used because hyperglycemia equivalently imposes adverse effects on every E9 embryos, a critical time point of neurulation occurring at E8-E10, before morphologically manifested in NTDs at E10 onwards.

Since JNK1/2 activation involves the induction of diabetic embryopathy and ASK1 leads to JNK1/2 activation, it is contemplated that ASK1 activation is responsible for maternal diabetes-induced NTDs (i.e., diabetic embryopathy). To determine if ASK1 deficiency in ASK1 knock-out (JNKS1KO) mice abrogates diabetic embryopathy, E11 embryos were isolated from NC, DM and diabetic ASK1KO (DM-ASK1KO) and examined for NTDs. In eleven DM-ASK1KO diabetic mice with total recovery of 68 embryos, average malformation rate was 2.81% and this malformation rate were significantly lower than that in embryos from DM mice (27.4%) while it was no significant difference when compared to the NC group (Table 1). Similar resorption rates were observed among the three groups, thus eliminating the possibility that the reduction of malformation rates in the DM-ASK1KO mice is due to the increase in embryo resorption. These data provide strong evidence that ASK1 is critically involved in the induction of diabetic embryopathy.

TABLE 1

Pregnancy outcomes at E11 in non-diabetic and diabetic WT and ASK1KO mice.

| Experimental groups | Total Embryos | Total malformed Embryos | Number of dams | resorption rates (%) | Malformation rates (%) |
|---|---|---|---|---|---|
| NC | 70 | 1 | 11 | 2.8 | 1.01 + 1.01 |
| DM | 71 | 19 | 11 | 4.2 | 27.4 + 3.18 |
| DM-ASK1KO | 68 | 2 | 11 | 2.9 | 2.81 + 1.89 |
| Non-diabetic ASK1KO | 63 | 1 | 8 | 1.6 | 1.3 + 1.25 |

Non-diabetic WT control (NC); Diabetic Mellitus WT (DM); Diabetic ASK1KO (DM-ASK1KO)

Example 6

An Agent of the Invention Decreases Embryo Malformation Rates

An agent of the invention (including, for example, an agent that modulates ASK1 activity, JNK activity, ERK activity, and Akt activity) is evaluated for its ability treat a diabetic embryopathy by using an experimental model described herein or one known by one of ordinary skill in the art. Briefly, starting from day 1 of pregnancy, diabetic rats are administered an agent of the invention whereas non-diabetic rats are not administered an agent of the invention. At E12, embryos are dissected out of uteri and evaluated for neural tube defects (NTDs), which is used as a measure of malformation rates (i.e., a measure of diabetic embryopathy).

Example 7

Non-human Primate Model of Diabetic Embryopathy

Non-human primates are closely related to humans with respect to physiology and pathophysiology. It is well accepted that the use of non-human primates in research, and the result obtained therefrom, can have a high correlation and applicability to humans. Considering this, the inventors of the present invention use non-human primates to determine the effectiveness of an agent of the invention to treat a diabetic embryopathy. The general scheme of using a non-human primate is discussed below. To determine the effectiveness of an agent of the invention, an agent is administered in a therapeutically effective amount.

Nonpregnant baboons (Papio anubis) housed in the primate colony existing at the University of Maryland School of Medicine, and weighing approximately 12 kg are untreated (n=5) or treated with Streptozotocin (STZ, 60 mg/kg body weight, iv, n=20) to induce type 1 diabetes. Glucose and glycosylated hemoglobin levels are assessed in blood samples (1 ml) collected daily (overnight fasting) after STZ administration and a glucose tolerance test conducted to confirm the diabetic state. Once hyperglycemia (serum glucose levels expected to exceed 500 mg/dl) and diabetes are induced, human insulin will be administered continuously via an osmotic pump inserted subcutaneously to maintain a euglycemic state (serum glucose levels of 80-100 mg/dl). 30 days after STZ treatment, untreated and insulin-treated type I diabetic baboons are paired with male baboons for 5 days at the periovulatory phase of the menstrual cycle and pregnancy confirmed by ultrasound at 20 days of gestation. Insulin will continue to be delivered to maintain a euglycemic state in pregnant baboons until day 20 of gestation.

Formation of the central nervous (i.e. neural tube) and cardiovascular (i.e. blood islands, cardiac primordium) systems begins at 22-28 days (i.e. 8-10%) of human gestation (Kurjak and Chervenak, 2003; Sadler, 1995) or 15-18 days of baboon gestation (term in baboons is 184 days). By 49 days (i.e. 18%) of human gestation or 33 days of baboon gestation the prosencephalon, mesencephalon and rhombencephalon of the brain and the atria, ventricles and septa of the heart have developed. By week 12 of human pregnancy (or day 60 of baboon pregnancy) neural and cardiovascular development is well advanced. The greatest risk of embryonic malformations (peak period of susceptibility to teratogenesis) occurs at 3-8 weeks of human gestation (Sadler, 1995, i.e. 8-20% of gestation or 15-37 days of baboon pregnancy).

Therefore, to expose the baboon embryo/fetus to hyperglycemia during the latter intervals, the rate of insulin delivery to the mother will be decreased to a level that elicits serum glucose levels of 300-500 mg/dl between days 20 and 60 of gestation. Day 20 is the earliest time that pregnancy can be detected in the baboon by ultrasonography. Between days 60 and 100 of gestation, insulin delivery will be restored to a level that maintains serum glucose at 80-100 mg/dl. The levels of glucose and glycosylated hemoglobin (to monitor euglycemic state) and PGF2α and malondialdehyde (biomarkers of oxidative stress and lipoperoxidation) are determined using maternal blood samples obtained at 1-2 day intervals throughout days 20-100. Fetal growth and organ system development are assessed by doppler ultrasonography at 10-day intervals between day 20 of gestation and the day of cesarean section.

The fetus and placenta are removed via cesarean section under isoflurance anesthesia on day 100 of gestation (i.e. midgestation). Day 100 is selected because embryonic/fetal development will be advanced (baboon fetal body weight approx 175 g) and the difficulty in carrying diabetic animals to term will be avoided. Since approximately 20% of the fetuses of diabetic pregnancies exhibit overt malformation, it is expected that 4 of the 20 diabetic baboons will show marked embryopathy. However, important data is expected to emerge from the remaining fetuses of diabetic animals that do not show obvious gross developmental malformation.

To determine that an agent of the invention is protective against diabetic embryopathy, an agent of the invention is administered to diabetic baboons to reduce or inhibit fetal malformation. Untreated (n=5) and STZ-treated (n=20) pregnant baboons are administered an agent of the invention daily by, for example, maternal subcutaneoudy injection between days 20 and 60 of gestation. The same parameters for assessment of fetal development throughout pregnancy and after cesarean section detailed herein are employed.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

REFERENCES

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety.

What is claimed is:

1. A method of treating a diabetic embryopathy comprising: administering to a pregnant mammal carrying an embryo or fetus having said embryopathy, an effective amount of at least one agent that modulates the activity of apoptosis signal-regulating kinase 1 (ASK1),
    wherein the at least one agent comprises at least one ASK1 inhibitor selected from the group consisting of thioredoxin; thioredoxin reductase; caspase-activated DNase (CAD) inhibitor; glutathione S-transferase mu; and an antagonist anti-ASK1 antibody.

2. The method of claim 1, wherein the at least one agent comprises an agent that decreases the activity of ASK1.

3. The method of claim 1, wherein the at least one agent comprises an agent that increases the activity of ASK1.

4. The method of claim 1, wherein said diabetic embryopathy comprises at least one abnormality, anomaly, or malformation of at least one body part or system selected from the group consisting of central nervous system, cardiovascular system, gastrointestinal tract, genitourinary system, skeletal system, face, eyes, ears, and skin.

5. The method of claim 1, wherein said administering comprises at least one method of administration selected from the group consisting of parenteral administration, epidural administration, and mucosal administration.

6. The method of claim 1, wherein said administering comprises at least one method of administration selected from the group consisting of intradermal, intramuscular, intraperitoneal, intravenous, subcutaneous, pulmonary, topical, injection, catheter, suppository, epidural, intranasal, rectal, vaginal, sublingual, buccal, oral, infusion, bolus injection, inhalation, insufflation, and implantation.

7. The method of claim 5, wherein said administration comprises at least one of method of administration selected from local and systemic administration.

8. A method of treating a diabetic embryopathy comprising administering to a pregnant mammal carrying an embryo or fetus having said embryopathy, an effective amount of at least one agent that modulates activity of a polypeptide involved in cell signaling that is altered during maternal diabetes or participates in the pathology of a diabetic embryopathy,
  wherein the at least one agent comprises at least one ASK1 inhibitor selected from the group consisting of thioredoxin; thioredoxin reductase; caspase-activated DNase (CAD) inhibitor; glutathione S-transferase mu; and an antagonist anti-ASK1 antibody.

9. The method of claim 8, wherein said mammal is human.

10. A method of treating a diabetic embryopathy comprising administering to a pregnant mammal carrying an embryo or fetus having said embryopathy, an effective amount of at least one agent that modulates activity of ASK, wherein the at least one agent comprises at least one ASK1 inhibitor selected from the group consisting of thioredoxin; thioredoxin reductase; caspase-activated DNase (CAD) inhibitor; glutathione S-transferase mu; and an antagonist anti-ASK1 antibody; and providing a multi-nutrient supplement regimen to the pregnant mammal.

* * * * *